(12) United States Patent
Lenting et al.

(10) Patent No.: US 6,313,081 B1
(45) Date of Patent: *Nov. 6, 2001

(54) DETERGENTS COMPRISING CELLULASES

(75) Inventors: Hermanus Bernardus Maria Lenting, VT Pijnacker; Rudolf Franciscus Wilhelmus Cornelis Van Beckhoven, EK Breda, both of (NL); Karl-Heinz Maurer, Erkrath (DE); Beatrix Kottwitz, Duesseldorf (DE); Albrecht Weiss, Langenfeld (DE); Pieter Van Solingen, VZ Naaldwijk (NL)

(73) Assignee: Henkel Kommanditgesellschaft auf Aktien (KGaA), Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,574

(22) PCT Filed: Apr. 26, 1995

(86) PCT No.: PCT/EP96/01755

§ 371 Date: Feb. 27, 1998

§ 102(e) Date: Feb. 27, 1998

(87) PCT Pub. No.: WO96/34092

PCT Pub. Date: Oct. 31, 1996

(30) Foreign Application Priority Data

Apr. 28, 1995 (EP) .................................................. 95201115

(51) Int. Cl.$^7$ ................................ C11D 3/386; D06L 1/12
(52) U.S. Cl. .......................... 510/320; 510/321; 510/392; 510/393; 510/530; 8/137; 435/209
(58) Field of Search ................... 435/209, 69.1; 8/115.56, 137; 510/392, 393, 530, 321, 320

(56) References Cited

U.S. PATENT DOCUMENTS

| | | | |
|---|---|---|---|
| 4,372,868 | 2/1983 | Saran et al. | 252/102 |
| 5,318,733 | 6/1994 | Carduck et al. | 264/15 |
| 5,382,377 | 1/1995 | Raehse et al. | 252/174 |
| 5,541,316 | 7/1996 | Engelskirchen et al. | 510/471 |
| 5,856,165 | 1/1999 | Van Solingen et al. | 435/209 |
| 6,063,611 | * 5/2000 | Van Solingen | 435/209 |

FOREIGN PATENT DOCUMENTS

| | | |
|---|---|---|
| 0 037 026 | 10/1981 | (EP) . |
| 0 220 016 | 4/1987 | (EP) . |
| 0 486 592 | 5/1992 | (EP) . |
| 0 636 740 | 2/1995 | (EP) . |
| 0 271 004 | 6/1998 | (EP) . |
| 2 075 028 | 11/1981 | (GB) . |
| 2 094 826 | 9/1982 | (GB) . |
| 2 095 275 | 9/1982 | (GB) . |
| WO91/17243 | 11/1991 | (WO) . |
| WO93/16110 | 8/1993 | (WO) . |
| WO95/02675 | 1/1995 | (WO) . |
| WO95/18219 | 7/1995 | (WO) . |

OTHER PUBLICATIONS

Tibtech 5: 255–261 (1987).
Anal. Biochem. 180:136–39 (1989).
Tenside Surf. Det. 30(1):388–393 (1993).
SÖFW 118: 483–99 (1992).
J. Bacter. 168(2):479–85, Undated.
Proc. Nat. Acad. Sci. 85: 2444–48 (1988).
Gene 93: 55–60 (1990).
Protein Engineering 1(1): 67–74 (1986).
Methods in Enzymology 160:59–74 (1988).
Findlay & Geisow (ed.), Protein sequencing– a practical approach, IRL Press (1989).
Analytical Biochemistry 47: 273–79 (1972).
Analytical Biochemistry 81: 21–27 (1977).

* cited by examiner

*Primary Examiner*—Lorna M. Douyon
(74) *Attorney, Agent, or Firm*—Wayne C. Jaeschke; Glenn E. J. Murphy

(57) ABSTRACT

A laundry detergent composition comprises a cellulase having a ratio of tensile strength loss to antipilling properties of less than 1. A method of laundering cotton-containing fabrics with the composition is also disclosed.

4 Claims, 2 Drawing Sheets

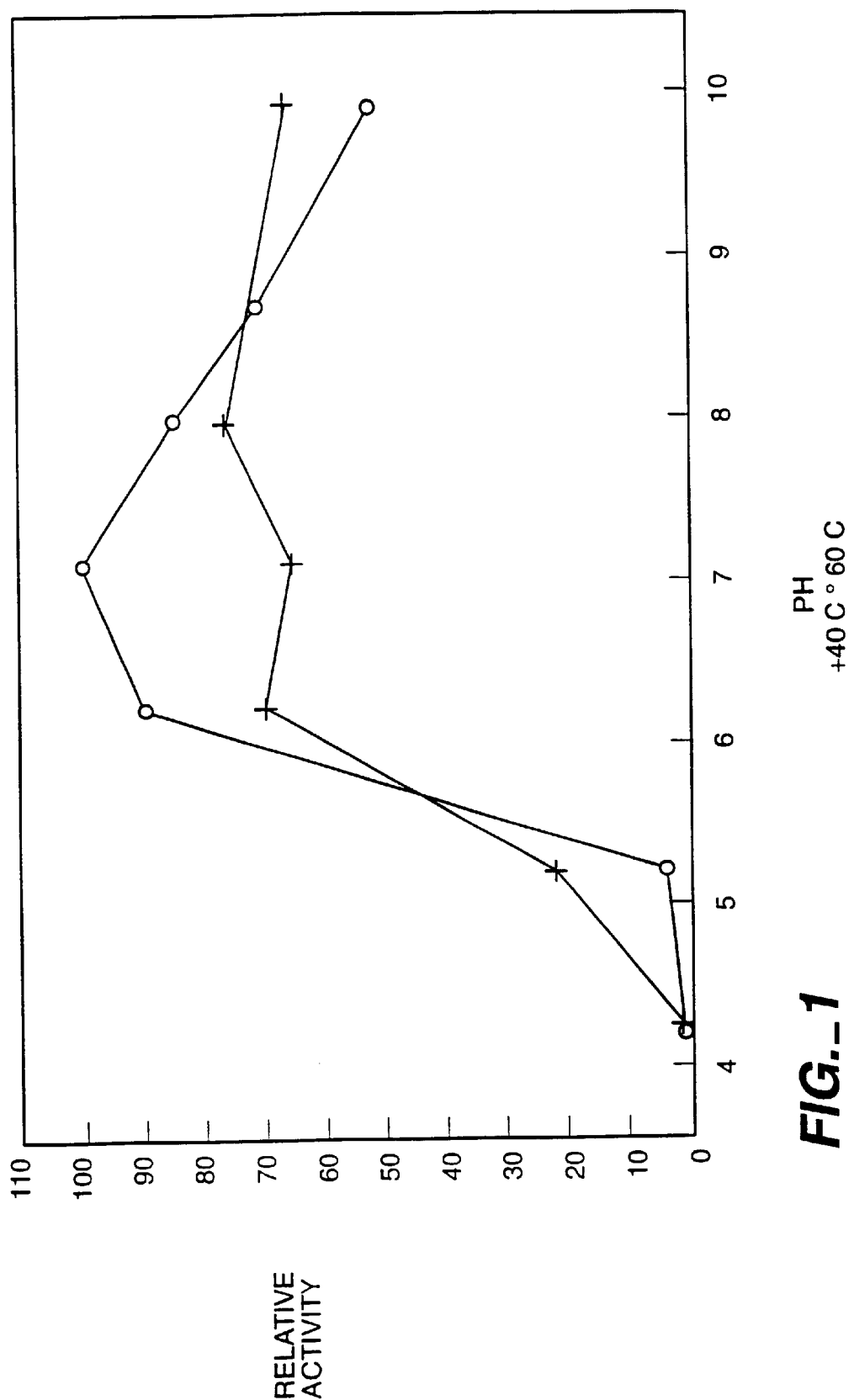
FIG._1

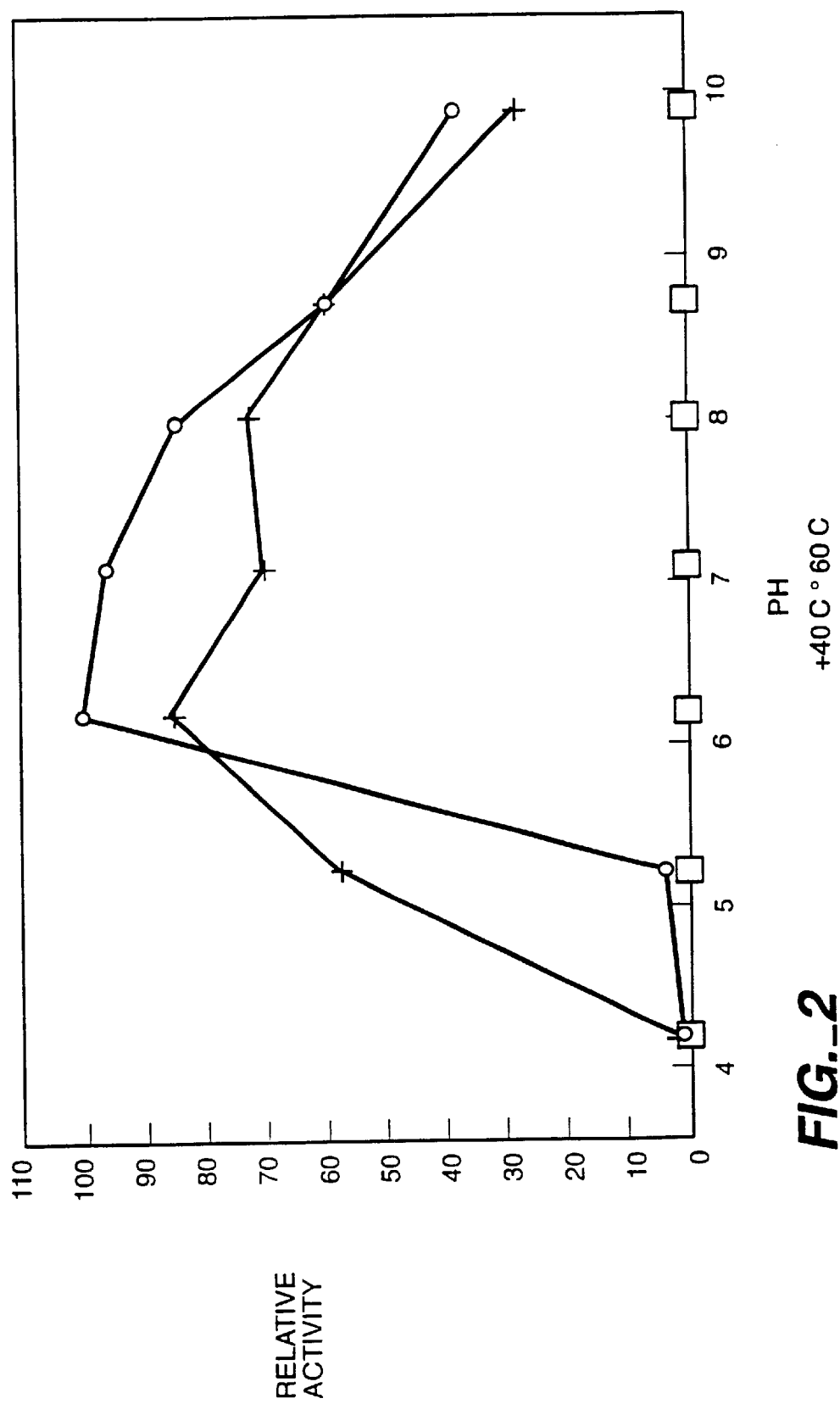
FIG._2

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 467 amino acids
      (B) TYPE: amino acid
      (C) STRANDEDNESS: single
      (C) TOPOLOGY: linear (ii) MOLECULE TYPE: protein (xi) SEQUENCE DESCRIPTION: SEQ ID NO: 1:

```
Met Lys Lys Ile Thr Thr Ile Phe Ala Val Leu Leu Met Thr Leu Ala
-26 -25              -20                 -15

Leu Phe Ser Ile Gly Asn Thr Thr Ala Ala Asp Asp Tyr Ser Val Val
                -10                  -5                   1       5

Glu Glu His Gly Gln Leu Ser Ile Ser Asn Gly Glu Leu Val Asn Glu
                 10              15                  20

Arg Gly Glu Gln Val Gln Leu Lys Gly Met Ser Ser His Gly Leu Gln
             25              30                  35

Trp Tyr Gly Gln Phe Val Asn Tyr Glu Ser Met Lys Trp Leu Arg Asp
         40              45              50
```

-continued

```
Asp Trp Gly Ile Thr Val Phe Arg Ala Ala Met Tyr Thr Ser Ser Gly
 55                  60                  65                  70

Gly Tyr Ile Asp Asp Pro Ser Val Lys Glu Lys Val Lys Glu Thr Val
 75                  80                  85

Glu Ala Ala Ile Asp Leu Gly Ile Tyr Val Ile Asp Trp His Ile
                 90                  95                 100

Leu Ser Asp Asn Asp Pro Asn Ile Tyr Lys Glu Ala Lys Asp Phe
            105                 110                 115

Phe Asp Glu Met Ser Glu Leu Tyr Gly Asp Tyr Pro Asn Val Ile Tyr
            120                 125                 130

Glu Ile Ala Asn Glu Pro Asn Gly Ser Asp Val Thr Trp Asp Asn Gln
            135                 140                 145                 150

Ile Lys Pro Tyr Ala Glu Val Ile Pro Val Ile Arg Asp Asn Asp
155                 160                 165

Pro Asn Asn Ile Val Ile Val Gly Thr Gly Thr Trp Ser Gln Asp Val
                170                 175                 180

His His Ala Ala Asp Asn Gln Leu Ala Asp Pro Asn Val Met Tyr Ala
            185                 190                 195

Phe His Phe Tyr Ala Gly Thr His Gly Gln Asn Leu Arg Asp Gln Val
    200                 205                 210

Asp Tyr Ala Leu Asp Gln Gly Ala Ala Ile Phe Val Ser Glu Trp Gly
    215                 220                 225                 230

Thr Ser Ala Ala Thr Gly Asp Gly Gly Val Phe Leu Asp Glu Ala Gln
235                 240                 245

Val Trp Ile Asp Phe Met Asp Glu Arg Asn Leu Ser Trp Ala Asn Trp
            250                 255                 260

Ser Leu Thr His Lys Asp Glu Ser Ser Ala Ala Leu Met Pro Gly Ala
            265                 270                 275

Asn Pro Thr Gly Gly Trp Thr Glu Ala Glu Leu Ser Pro Ser Gly Thr
            280                 285                 290

Phe Val Arg Glu Lys Ile Arg Glu Ser Ala Ser Ile Pro Pro Ser Asp
            295                 300                 305                 310

Pro Thr Pro Pro Ser Asp Pro Gly Glu Pro Asp Pro Gly Glu Pro Asp
315                 320                 325

Pro Thr Pro Pro Ser Asp Pro Gly Glu Tyr Pro Ala Trp Asp Ser Asn
                330                 335                 340

Gln Ile Tyr Thr Asn Glu Ile Val Tyr His Asn Gly Gln Leu Trp Gln
            345                 350                 355

Ala Lys Trp Trp Thr Gln Asn Gln Glu Pro Gly Asp Pro Tyr Gly Pro
            360                 365                 370

Trp Glu Pro Leu Lys Ser Asp Pro Asp Ser Gly Glu Pro Asp Pro Thr
    375                 380                 385                 390

Pro Pro Ser Asp Pro Gly Glu Tyr Pro Ala Trp Asp Ser Asn Gln Ile
395                 400                 405

Tyr Thr Asn Glu Ile Val Tyr His Asn Gly Gln Leu Trp Gln Ala Lys
                410                 415                 420

Trp Trp Thr Gln Asn Gln Glu Pro Gly Asp Pro Tyr Gly Pro Trp Glu
            425                 430                 435

Pro Leu Asn
        440
```

(2) INFORMATION FOR SEQ ID NO:2:

(i) SEQUENCE CHARACTERISTICS:
        (A) LENGTH: 574 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO: 2:

```
Met Lys Trp Met Lys Ser Met Val Trp Leu Ala Val Val Leu Val Val
1               5                   10                  15

Ser Phe Val Ala Pro Ala Val Ser Ser Ala Asn Glu Asp Val Lys Thr
            20                  25                  30

Leu Asp Ile Gln Ser Tyr Val Arg Asp Met Gln Pro Gly Trp Asn Leu
            35                  40                  45

Gly Asn Thr Phe Asp Ala Val Gly Gln Asp Glu Thr Ala Trp Gly Asn
50                      55                  60

Pro Arg Val Thr Arg Glu Leu Ile Glu Arg Ile Ala Asp Glu Gly Tyr
65                  70                  75                  80

Lys Ser Ile Arg Ile Pro Val Thr Trp Glu Asn Arg Ile Gly Gly Ala
            85                  90                  95

Pro Asp Tyr Pro Ile Asp Pro Gln Phe Leu Asn Arg Val Asp Glu Val
            100                 105                 110

Val Gln Trp Ala Leu Glu Glu Asp Leu Tyr Val Met Ile Asn Leu His
        115                 120                 125

His Asp Ser Trp Leu Trp Ile Tyr Glu Met Glu His Asn Tyr Asn Gly
130                 135                 140

Val Met Ala Lys Tyr Arg Ser Leu Trp Glu Gln Leu Ser Asn His Phe
145                 150                 155                 160

Lys Asp Tyr Pro Thr Lys Leu Met Phe Glu Ser Val Asn Glu Pro Lys
            165                 170                 175

Phe Ser Gln Asn Trp Gly Glu Ile Arg Glu Asn His His Ala Leu Leu
            180                 185                 190

Asp Asp Leu Asn Thr Val Phe Phe Glu Ile Val Arg Gln Ser Gly Gly
            195                 200                 205

Gln Asn Asp Ile Arg Pro Leu Val Leu Pro Thr Met Glu Thr Ala Thr
            210                 215                 220

Ser Gln Pro Leu Leu Asn Asn Leu Tyr Gln Thr Ile Asp Lys Leu Asp
225                 230                 235                 240

Asp Pro Asn Leu Ile Ala Thr Val His Tyr Tyr Gly Phe Trp Pro Phe
            245                 250                 255

Ser Val Asn Ile Ala Gly Tyr Thr Arg Phe Glu Glu Asp Ser Lys Arg
            260                 265                 270

Glu Ile Ile Glu Thr Phe Asp Arg Val His His Thr Phe Val Ala Arg
            275                 280                 285

Gly Ile Pro Val Val Leu Gly Glu Phe Gly Leu Leu Gly Phe Asp Lys
            290                 295                 300

His Thr Gly Val Ile Gln Gln Gly Glu Lys Leu Lys Phe Phe Glu Tyr
305                 310                 315                 320

Leu Ile His His Leu Asn Glu Arg Asp Ile Thr His Met Leu Trp Asp
            325                 330                 335

Asn Gly Gln His Phe Asn Arg His Thr Tyr Glu Trp Tyr Asp Glu Glu
            340                 345                 350

Leu Phe Asp Met Leu Arg Ala Ser Trp Gly Gly Arg Ser Ser Val Ala
            355                 360                 365

Glu Ser Asn Phe Ile Tyr Leu Lys Gln Gly Asp Arg Ile Ala Asp Ala
370                 375                 380
```

```
Thr Val Thr Leu Gln Leu His Gly Asn Glu Leu Thr Gly Leu Gln Ala
385                 390                 395                 400

Asn Gly Gln Arg Leu Thr Pro Gly Gln Asp Tyr Glu Leu Asn Gly Glu
            405                 410                 415

Arg Leu Thr Val Lys Ala His Val Leu Ser Ala Ile Ala Gly Ser Gly
            420                 425                 430

Thr Leu Gly Thr Asn Gly Met Val Thr Ala Glu Phe Asn Arg Gly Ala
        435                 440                 445

Asp Trp His Phe Arg Val Asn Thr Tyr Arg Thr Pro Val Leu Gln Ser
    450                 455                 460

Thr Gln Gly His Val Ser Asn Phe Ser Ile Pro Ala Ser Phe Asn Gly
465                 470                 475                 480

Asn Ser Leu Ala Thr Met Glu Ala Val Tyr Val Asp Gly Gly Asn Ala
            485                 490                 495

Gly Pro Gln Asp Trp Thr Ser Phe Lys Glu Phe Gly Tyr Ala Phe Ser
            500                 505                 510

Pro Ser Tyr Asp Thr His Glu Ile Lys Leu Thr Glu Ala Phe Phe Arg
            515                 520                 525

Glu Val Arg Asp Gly Glu Val Arg Leu Thr Phe His Phe Trp Ser Gly
        530                 535                 540

Glu Ile Val Asn Tyr Thr Ile Ile Lys Asn Gly Asn Gln Val Thr Gly
545                 550                 555                 560

Ile Ala Ala Gln Thr Thr Asn Ser Lys Asn Lys Asn Lys Lys
            565                 570
```

DETERGENTS COMPRISING CELLULASES

BACKGROUND OF THE INVENTION

1. Field of the Invention

The present invention relates to the use of novel cellulases with improved properties in detergents and aqueous laundry solutions. The invention further relates to detergents and detergent additives comprising the novel cellulase.

2. Discussion of the Related Art

Cellulases, also called cellulolytic enzymes, are enzymes which are capable of the hydrolysis of the β-D-glucosidic linkages in celluloses. Cellulolytic enzymes have been divided traditionally into three classes: endoglucanases, exoglucanases or cellobiohydrolases and β-glucosidases (Knowles, J. et al. (1987), TIBTECH 5, 255–261). Cellulolytic enzymes can be produced by a large number of bacteria, yeasts and fungi. Microorganisms that produce cellulases are described in for example GB-A-2094826.

Several applications have been developed for the use of cellulolytic enzymes:

- degrading (wood) cellulose pulp into sugars for (bio) ethanol production;
- several textile treatments like 'stone washing' and 'biopolishing';
- application in detergent compositions.

The use of cellulases in detergent compositions started with cellulases capable of reducing the harshness, i.e. softening of cotton containing fabrics, as described in for example GB-B-1358599.

It is further known that detergent compositions comprising cellulases are effective in removing dirt, i.e. cleaning. The efficiency of cellulolytic enzymes, cellulases, in terms of cleaning textile has been recognized for some time. GB-A-2075028, GB-A-2095275 and GB-A-2094826 disclose detergent compositions with cellulase for improved cleaning performance.

It is also known in the art that cellulases can act as a colour clarifying agent in laundry detergents. After repeated washing of soiled fabrics, cotton containing fabrics appear to be greyish, most probably due to disrupted fibres caused by mechanical action. The fibres are torn up resulting in disordered fibres which are broken. The use of cellulases as colour clarification agents for coloured fabrics has been described in EP-A-0220016. Actually cellulase mixtures from the fungal strain Humicola insolens (DSM 1800) are commonly used in detergents to result in antipilling and colour revival properties. The cellulolytic enzyme system produced by the wild type microorganism is available under the trade name of Celluzyme® by Novo-Nordisk. In addition a cloned (single) cellulase from the same origin under the trade name Carezyme® is also used in detergents.

The main disadvantage of the cellulases known in the art showing colour clarification is that these enzymes aggressively degrade the cellulose containing fabrics which results in damage by undesirable loss of tensile strength of the fabrics.

On the other hand cellulases known in the art showing good cleaning properties show hardly any colour clarification effects. The first commercial detergent with cellulases in the world contained a bacterial cellulase. This enzyme represents an above mentioned alkaline endoglucanase from a Bacillus species that does not attack cellulose fibres. The enzyme is described to give a cleaning effect during washing. No effects with respect to anti-pilling or colour revival have been described for this enzyme.

From the above it will become clear that it is still desirable to provide for improved cellulases in detergent applications. Using mixtures of cellulases, as suggested in international patent application WO-A-95/02675, is supposed to provide the above mentioned performance in laundry washing, but to our knowledge, it has not previously been possible to use single enzymes providing all these characteristics when applied in laundry washing.

BRIEF DESCRIPTION OF THE DRAWINGS

FIG. 1 shows the relative activities of the cellulase BCE 103. In Example 1, this figure is referred to as the pH/temperature profiles. All activities for both 40° C. and 60° C. are related to the highest activity fixed at 100%.

FIG. 2 shows the relative activities of the cellulase BCE 113.

DESCRIPTION OF THE INVENTION

Surprisingly it has been found that the use of certain single cellulases which are capable of cleaning, antiredeposition, colour clarification and antipilling performance in laundry washing does not at all result in unacceptable damage to the textiles washed.

Accordingly, the present invention relates to the use of a single cellulase with a ratio of tensile strength loss (TSL, as herein defined) to antipilling properties (AP, as herein defined) below 1 in aqueous laundry solutions.

To measure tensile strength loss is a way to measure damage caused by mechanical stress of enzymatical action on fibers. It is to be understood that for the purpose of the present invention cotton fiber has to be used. The method measures the tensile strength of single fibers under wet conditions. It is described in German Standard DIN 53, 857, part 1 as well as in the International Standard ISO 2267.

As the effect normally shows up in a significant amount only after about 20 to 25 wash cycles, there is always some tensile strength loss due to the mechanical forces acting on the cotton fiber during the washing process. Therefore the tensile strength loss of a control fabric washed without cellulases using the same formulation of detergent and the same type of washing machine and washing programme has to be subtracted. To calibrate the values, a preparation of the (single) endoglucanase V from Humicola insolens (EG V) in equal amounts of enzymatic protein in the detergent is used as a standard and the value of the tensile strength loss for this sample minus the control value of detergent without cellulase is taken as a TSL of 100%. This cellulase EG V has been described for example in the international patent application WO 91/17243. The amount of protein can be measured for example by using the BCA Pierce method as described by R. E. Brown et al. in Anal. Biochem. 1989, vol. 180, p. 136–139.

A preparation of an above mentioned Bacillus cellulase available from Kao Corp. under the trade mark KAC® 500 or KAC® 700 may be used as comparison, resulting in general in a very low tensile strength loss as compared to the control washing experiment with no cellulase present.

The attack of cellulases on protruding microfibrils, pills and cotton fluff on the surface of a cotton fabric results in an optically visible removal of that pills. To test the effect, washings are to be performed using a detergent with and without cellulase, as described for the detremination of TSL. The antipilling effect, too, can best be seen after an increasing number of wash cycles. Therefore a number of 15 to 40 wash cycles are generally used to demonstrate this effect of cellulases.

There are three different methods that can be used for quantification of this effect:
1. visual evaluation by a test group (panel)
2. measurement of light reflection (L-value of the CIELAB-system)
3. determination of the cotton fluffs by means of optical measurement The determination using the L-value of the CIELAB-system [Commission Internationale de l'Éclairage] was described by U. Hotz in Tenside Surf. Det. 1993, vol. 30, page 388. The optical measurement system, which is used in the preferred method of determining the antipilling properties, usually consists of a light source, a microscope tube and a CCD colour camera recording the light reflected from the surface of a fabric. Depending on the amount of pills and fluff on the surface of the fabric the amount of reflected light as measured by digital image analysis changes. Such a system can be used to measure quantitatively the amount of pill and fluff on fabrics, normally after 15 to 40 wash cycles depending on the type and activity of the cellulase added to the detergent. An optical system which can be used to measure the degree of pilling has been described by T. Müller-Kirschbaum and H. Grundmann in S ÖFW, vol. 118 (1992), p. 483–499.

Whatever method is used to determine the antipilling effect of the cellulase to be tested, the standard cellulase EG V has to be tested under the same conditions and its effect has to be determined by the same method, taking into account the value resulting from the use of the detergent without cellulase. The value obtained for EG V is taken as AP=100%.

As can be seen from this definition, the known cellulase EG V from Humicola insolens has a ratio of TSL to AP of 1. As the above mentioned Bacillus cellulase available from Kao Corp. under the trade mark KAC® 500 or KAC® 700 has a low AP and a very low TSL, it can be seen that also the ratio for this cellulase is approximately 1. Cellulases which may be used according to the invention, especially in detergents, have a ratio of TSL to AP as much as possible below 1, preferably below 0.8 and more particularly in the range of 0.001 to 0.5. A ratio of TSL to AP of for example 0.5 means that only 50% of tensile strength loss is seen at an enzyme concentration yielding the same antipilling effect as the standard cellulase.

The aqueous laundry solution preferably comprises cellulase according to the definition given above in concentrations of 0.01 mg/l to 0.2 mg/l, more particularly 0.015 mg/l to 0.1 mg/l. These concentrations refer to the weight of cellulolytic protein. In addition all ingredients normally found in laundry solutions can be present.

Another aspect of the present invention is the use of a single cellulase with a ratio of TSL to AP below 1 to provide an anti-greying effect to fabrics, especially coloured fabrics.

In another aspect of the invention a single cellulase with a ratio of TSL to AP below 1 is used to provide a softening effect to fabrics.

The present invention also relates to the use of a single cellulase with a ratio of TSL to AP below 1 to provide colour clarification or to inhibit colour deterioration of fabrics, especially coloured fabrics.

The present invention further relates to the use of single cellulase with a ratio of TSL to AP below 1 to inhibit the wrinkling of fabrics and to ease the ironing of fabrics.

We found that the use of a single cellulase according to the definition of the invention, unlike previously known mixtures of cellulases which provide colour clarification, does not degrade cotton to an undesirable level causing tensile strength loss.

It is further found that in using a cellulase of the definition according to the invention, unlike previously known cellulases which provide colour clarification, the enzyme does not accumulate on the fabric after repeated laundry washing.

In another aspect, the invention is directed to detergent compositions, detergent additives and fabric softener compositions comprising a single cellulase according to the definition given above.

As noted before, the present invention generally relates to the use of novel cellulases. However, prior to disclosing this invention in more detail, the following terms will be defined.

„Cellulase" is a generic name for enzymes acting on cellulose and its derivatives, and hydrolysing them into glucose, cellobiose or cellooligosaccharides.

The term „single" cellulase used herein is intended to mean a cellulase which is produced by one gene.

„Obtainable form" an organism in connection with a cellulase means that such cellulase has an amino acid sequence which corresponds to the amino acid sequence of a cellulase which may be obtained from that organism.

„Derivative" is intended to indicate a protein which is derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or more sites in the amino acid sequence, or insertion of one or more amino acids at one or more sites in the native amino acid sequence. The preparation of a derivative is usually achieved by modifying a DNA sequence which encodes for the native protein, transformation of that DNA sequence into a suitable host and expression of the modified DNA sequence to form the derivative protein. The derivative of the invention includes peptides comprising altered amino acid sequences in comparison with a precursor enzyme amino acid sequence (e.g., a wild type or native state enzyme according to the present invention) and which peptides retain a characteristic enzyme nature of the precursor enzyme but which have altered properties in some specific aspect. For example, an altered cellulase may have an increased pH optimum or increased temperature resistance but will retain its characteristic cellulase activity. Derivatives also includes chemical modifications of amino acid residues within the enzyme molecule.

„Host cell" means a cell which has the capacity to act as a host and expression vehicle for a recombinant DNA vector comprising DNA which encodes for the native protein or a derivative.

The term „cleaning" means the removal of dirt attached to laundry.

The term „pilling" in this respect is the formation of pills and fuzz on the surface of cotton containing fabrics due to broken or disordered fibres.

The term „antipilling" is used to describe the prevention of the formation of pills and fuzz on the surface of cotton containing fabrics as well as the removal of pills and fuzz from cotton containing fabrics. Antipilling normally results in colour clarification when coloured cotton containing fabrics are treated.

The term „color clarification" in this respect is the reestablishment of the attractive fresh look of coloured fabrics containing or consisting of cellulose based fibres, which have developed a greyish appearance by treatment, especially with laundry detergents, of the coloured fabric.

The term „redeposition" in this respect is deposition of dirt or colour components that were removed from these textiles or fabrics during a laundry washing or textile treatment.

The term "antiredeposition" in this respect is the action of cellulase to prevent or diminish the redeposition of dirt and colour components on the fabric.

By a "laundry solution" is meant an aqueous solution used for washing, rinsing or conditioning, e.g. softening, fabrics.

In a preferred aspect, the present invention relates to the use of a cellulase which is obtainable from microorganisms which are deposited according to the Budapest Treaty on the International Recognition of the Deposits of Microorganisms for the Purposes of Patent Procedures, at the Central Bureau voor Schimmelcultures, Baam, The Netherlands on Dec. 23, 1993 under deposition numbers CBS 669.93 and CBS 670.93 (described in international patent application WO-A-95/18219). This strains have been classified as new species of the genus Bacillus, which do not belong to any of the presently known rRNA-groups of Bacillus. As used herein, the deposited species will be referred to as CBS 669.93 and CBS 670.93.

The microorganisms may be obtained for example from water and soil samples collected in alkaline environments such as alkaline soils and soda lakes.

The microorganisms have subsequently been screened using a carboxymethyl cellulose (CMC)-agar diffusion assay. Strains which showed a clearing zone in this test were isolated as potential cellulase producing strains. Genomic gene libraries of the alkali tolerant cellulase producing strains were constructed. Recombinant clones were screened by agar diffusion on CMC-agar. Recombinant clones that showed clearing zones around the colony were isolated. Single cellulases were produced by fermentation of the recombinant clones in 4*YEP-medium for 48 hours at 30° C. The obtained single cellulases, optionally purified as described in Example 1, were tested in the tests defined above to measure TSL and AP.

Surprisingly it was found that the cellulase obtainable from CBS 670.93 or CBS 669.93 show a good performance in both tests and have a ratio of TSL to AP below 1.

In a preferred embodiment of the invention, an approximately 50 kD cellulase (calculated on the basis of the amino acid sequence (SEQ ID NO:1) of the mature protein) derived from CBS 670.93 (referred to as "BCE 103" herein) is used. It has been revealed by analyzing the gene encoding the amino acid sequence of the approximately 50 kD cellulase that this cellulase is 89% identical in sequence and 92.5% similar in sequence to the cellulase CelA of Bacillus sp. N-4 (Fukumori et al., J. Bacter., vol. 168, pp. 479–485) by using the TFastA program (Sequence Analysis Software Package 6.0 of Genetic Computer Group, University of Wisconsin, Biotechnology Center, Madison, Wis.) as described by Pearson and Lipman in Proc. Nat. Acad. Sci., vol. 85, pp. 2444–2448 (1988). The amino acid sequence of BCE 103 is given in SEQ. ID. NO:1. The present invention further encompasses the use of cellulases with an amino acid sequence which have greater than 89%, preferably greater than 95% sequence identity and/or greater than 92.5%, preferably greater than 97% sequence similarity thereto, and detergents comprising such a cellulase.

In an equally preferred embodiment, an approximately 63 kD cellulase (calculated on the basis of amino acid sequence of the mature protein) derived from CBS 669.93 (referred to herein as "BCE 113") is used. It has been revealed by analyzing the gene encoding the amino acid sequence of the approximately 63 kD cellulase that this cellulase is 58% identical in sequence and 72% similar in sequence to the cellulase CelB of Bacillus lautus (Jorgensen et al, Gene, vol. 93 (1990), p. 55–60) by using the TFastA program (Sequence Analysis Software Package 6.0 of Genetic Computer Group, University of Wisconsin, Biotechnology Center, Madison, Wis.) as described by Pearson and Lipman in Proc. Nat. Acad. Sci., vol. 85 (1988), p. 2444–2448. The amino acid sequence of BCE 113 is given in SEQ ID NO:2. The present invention further encompasses the use of cellulases with an amino acid sequence which have greater than 58%, preferably greater than 80% and more particularly greater than 90% sequence identity and/or greater than 72%, preferably greater than 80% and more particularly greater than 90% sequence similarity thereto, and detergents comprising such a cellulase. A cellulase which may be used in detergents according to the present invention in addition to having a ratio of TSL to AP below 1 usually performs well in the Antiredeposition Test as described in Example 4. Whiteness maintenance of white fabric is measured by a reflectance measurement. The higher the reflectance value, the more effective the tested cellulase is in antiredeposition performance. They also perform well in the Softening Test as described in Example 4. Depilling is the removal of fibrils and/or microfibers that are disordered and/or broken which usually make a coloured cotton containing fabric look greyish. The more disordered and/or broken fibrils are removed the better the coloured cotton containing fabrics look. Depilling effectiveness can be judged by panels or can be quantified by an image analysis system, as specified above for the measurement of AP. Cellulases which fulfil the requirement of the ratio defined above usually exhibit the following properties: They show a delta REM of at least 4 units, preferably at least 5 units, in the Anti Redeposition Test as defined in the Examples, and they show a depilling result which is at least comparable to that of the cellulase obtainable from CBS 670.93.

The cellulases which can be used according to the present invention may be produced by a process which can be developed using genetic engineering. As a first step the gene encoding the cellulase of the present invention can be cloned using λ-phage (expression) vectors and E. coli host cells. Alternatively PCR cloning using consensus primers designed on conserved domains may be used. Expression of the gene encoding the cellulase of the present invention in E. coli is shown to give an active protein.

After a first cloning step in E. coli, a cellulase gene can be transferred to a more preferred industrial expression host such as Bacillus or Streptomyces species, a filamentous fungus such as Aspergillus, or a yeast. High level expression and secretion obtainable in these host organisms allow accumulation of the cellulase of the invention in the fermentation medium from which they can subsequently be recovered.

Cellulases according to the invention are preferably used in amounts of $8·10^{-5}\%$ by weight (0.8 ppm) to $8·10^{-3}\%$ by weight (80 ppm), more particularly $1·10^{-4}\%$ by weight (1 ppm) to $4·10^{-3}\%$ by weight (40 ppm), referring to the celluloytic protein, in detergents. Detergent compositions comprising a cellulase defined according to the invention may additionally comprise surfactants which may be of the anionic, non-ionic, cationic, amphoteric or zwitterionic type as well as mixtures of these surfactant classes. Detergent compositions of the invention may contain other detergent ingredients known in the art, as e.g. builders, bleaching agents, bleach activators, anti-corrosion agents, sequestering agents, soil release polymers, perfumes, other enzymes, enzyme stabilizers, etc.

Suitable binders are in particular those from the classes of polycarboxylic acids, more particularly polymeric acrylic acids, methacrylic acids, maleic acids, copolymers thereof and oxidized carbohydrates, as described in international patent application WO-A-93/16110, layer silicates, more particularly bentonites, alumosilicates, more particularly zeolites, crystalline or amorphous alkali metal silicates, more particularly sodium silicates, and alkali metal carbonates, more particularly sodium carbonate. The polycarboxylic acids mentioned are normally used in the form of their alkali metal salts, more particularly in the form of their sodium or potassium salts. The zeolites preferably incorporated are in particular those of the A, P or X type or mixtures thereof. Preferred alkali metal silicates are those with molar ratios of $SiO_2$ to alkali metal oxide of 1.5 to 3.0. Builders such as these are preferably present in detergents according to the invention in quantities of 20% by weight to 80% by weight.

Nonionic surfactants may be present in the detergents according to the invention, preferably in quantities of not more than 10% by weight and, more preferably, in quantities of 2% by weight to 6% by weight, based on the detergent as a whole. Suitable nonionic surfactants are alkyl polyglycosides containing 10 to 22 carbon atoms in the alkyl component and alkoxylates, particularly ethoxylates and/or propoxylates, of linear or branched $C_{10-22}$ and preferably $C_{12-18}$ alcohols. The degree of alkoxylation of the alcohols is between 1 and 20 and preferably between 3 and 10. They may be prepared in known manner by reaction of the corresponding alcohols with the corresponding alkylene oxides. The fatty alcohol derivatives are particularly suitable, although their branched-chain isomers, more particularly so-called oxoalcohols, may be used for the production of useable alkoxylates. Accordingly, the ethoxylates of primary alcohols containing linear dodecyl, tetradecyl, hexadecyl or octadecyl radicals and mixtures thereof are particularly useful. In addition, corresponding ethoxylation and/or propoxylation products of alkyl amines, vicinal diols and carboxylic acid amides, which correspond to the alcohols mentioned in regard to the alkyl component, and of alkyl phenols containing 5 to 12 carbon atoms in the alkyl component may also be used. Suitable anionic surfactants are in particular those of the sulfate or sulfonate type, although other types, such as soaps, long-chain N-acyl sarcosinates, salts of fatty acid cyanamides or salts of ether carboxylic acids, which may be obtained from long-chain alkyl or alkyl phenyl polyglycol ethers and chloroacetic acid, may also be used. The anionic surfactants are preferably used in the form of the sodium salts. Surfactants are preferably present in quantities of 2% by weight to 30% by weight and more preferably in quantities of 5% by weight to 20% by weight.

Particularly suitable surfactants of the sulfate type are the sulfuric acid monoesters of long-chain primary alcohols of natural and synthetic origin containing 10 to 20 carbon atoms, i.e. the sulfuric acid monoesters of fatty alcohols such as, for example, coconut oil fatty alcohols, tallow fatty alcohols, oleyl alcohol, or the $C_{10-20}$ oxoalcohols and those of secondary alcohols of the same chain length. The sulfuric acid monoesters of aliphatic primary alcohols, secondary alcohols and alkyl phenols ethoxylated with 1 to 6 mol ethylene oxide are particularly suitable. Sulfated fatty acid alkanolamides and sulfated fatty acid monoglycerides are also suitable.

The sulfonate-type surfactants are primarily the alkylbenzene sulfonates containing $C_{9-15}$ alkyl groups, sulfosuccinic acid monoesters and diesters containing 6 to 22 carbon atoms in the alcohol components and the esters of a-sulfofatty acids, for example the a-sulfonated methyl or ethyl esters of hydrogenated coconut oil, palm kernel oil or tallow fatty acids. Other suitable surfactants of the sulfonate type are the alklane sulfonates obtainable from $C_{12-18}$ alkanes by sulfochlorination or sulfoxidation and subsequent hydrolysis or neutralization or by addition of bisulfite onto olefins and also olefin sulfonates, i.e. mixtures of alkene and hydroxyalkane sulfonates and also disulfonates which are obtained, for example, from long-chain monoolefins with a terminal or internal double bond by sulfonation with gaseous sulfur trioxide and subsequent alkaline or acidic hydrolysis of the sulfonation products.

Bleaching agents are preferably selected from the type containing peroxygen, as hydrogen peroxide, alkali perborate, alkali percarbonate, alkali persilicate and/or alkali persulfate. Particularly preferred are sodium perborate monohydrate and sodium percarbonate. Bleaching agents may be present in amounts of 5% by weight to 25% by weight, more particularly 7% by weight to 20% by weight.

Bleach activator compounds include in particular N- or O-acyl compounds, for example polyacrylated alkylene diamines, more particularly tetraacetyl ethylene diamine, N-acrylated triazines, more particularly 1,5-diacetyl-2,4-dioxohexahydro-1,3,5-triazine, acylated glycolurils, more particularly tetraacetyl glycoluril, N-acylated hydantoins, hydrazides, triazoles, urazoles, diketopiperazines, sulfuryl amides and cyanurates, also carboxylic anhydrides, more particularly phthalic anhydride, carboxylic acid esters, more particularly sodium isononanoyloxy benzene sulfonate, and acylated sugar derivatives, more particularly pentaacetyl glucose. The bleach activator may be coated in the usual way with shell-forming substances or may be granulated, optionally using granulation aids, and if desired may contain other additives, for example dye. A bleach activator which forms peroxycarboxylic acids with 2 to 12 carbon atoms, in particular peroxoacetic acid, under the washing conditions is preferably used. A particularly preferred bleach activator is tetraacetyl ethylene diamine (TAED) granulated with carboxymethyl cellulose with average particle sizes of 0.01 mm to 0.8 mm, which may be produced by the process described in European Patent EP-B-0 037 026. In addition to the above mentioned bleach activators or even substituting them so-called bleach catalysts may be used, which are transition metal complexes, for example as described in Enzymes which may be present in the detergents according to the invention, in addition to the cellulase according to the definition, are proteases, lipases, cutinases, amylases, pullulanases, other cellulases, hemicellulases, xylanases, oxidases and/or peroxidases. They may be present in amounts up to 5% by weight, preferably 0.2% by weight to 2% by weight.

The detergent compositions of the invention may be formulated in any convenient form e.g. as a powder or liquid. For the production of detergents with high apparent density of e.g. 650 g/l to 950 g/l a method using an extrusion step, as described in European patent EP-B-0 486 592, is preferred.

Fabric softening compositions comprising the inventive cellulase may comprise further to this cellulase cationic surfactants, preferably of the so-called esterquat type, which are capable of fabric softening and which may increase the fabric softening properties of the compositions.

EXAMPLES

Example 1

Production of Cellulases

Screening for cellulase producing microorganisms

Two methods were applied for the isolation of cellulase-producing microorganisms:

1) the soil and water samples were suspended in 0.85% saline solution and directly used in the carboxymethyl cellulose (CMC)-agar diffusion assay for detection of cellulase producing colonies.
2) The soil and water samples were enriched for cellulase containing strains by incubation in a cellulose containing liquid minimal medium or GAM-medium for 1 to 3 days at 40° C. Cultures that showed bacterial growth were analyzed for cellulase activity using the CMC-agar diffusion assay for detection of cellulase producing colonies.

Isolation of alkalitolerant, cellulase producing strains

Strains that showed clearing zones in the agar diffusion assay were fermented in 25 milliter GAM-medium in 100 milliliter shake flasks in an Incubator Shaker (New Brunswick Scientific, Edison, N.J., USA), at 250 r.p.m. at 40° C. for 72 hours. CMCase activity was determined in the culture broth at pH 9 and 40° C.

Isolation of cellulase genes

Genomic gene libraries of the alkalitolerant cellulase producing strains were constructed in plasmid pTZ18R (Mead, D. A., et al. (1986) Protein Engineering 1, 67). Recombinant clones were screened by agar diffusion of CMC-agar as described by Wood, P. J., et al. (1988) Methods in Enzymology 160, 59–74. Strains that showed clearing zones around the colony were isolated. The CMCase activity of the recombinant strains was determined after fermentation for 48 hours at 30° C. in 4*YEP-medium. The plasmid DNA of the recombinant strains was isolated and the inserts were characterized by restriction enzyme analysis and nucleotide sequence analysis.

Media

The minimal medium (pH 9.7) using in the CMC-agar diffusion assay and the enrichment procedure, consisted of $KNO_3$ 1%, Yeast extract (Difco) 0.1%, $KH_2PO_4$ 0.1%, $MgSO_4.7H_2O$ 0.02%, $Na_2CO_3$ 1%, NaCl 4% and 0.25% CMC (Sigma C-4888). For solidification 1.5% agar was added.

The complex medium (GAM) used for enzyme production of the donor strains consisted of Peptone (Difco) 0.5%, Yeast extract (Difco) 0.5%, Glucose.$H_2O$ 1%, $KH_2PO_4$ 0.1%, $MgSO_4.7H_2O$ 0.02%, $Na_2CO_3$ 1%, NaCl 4%. The pH was adjusted to 9.5 with 4M HCl after which 1% CMC was added.

The complex medium (4*YEP) used for the enzyme production in E. coli recombinant strains consisted of Yeast extract (Difco) 4%, Peptone (Difco) 8%, lactose 0.2%, 100 µg/ml ampicilline.

CMC-agar diffusion assay for colonies

Cell suspensions in 0.85% saline solution were plated on CMC-containing minimal medium. After incubation for 1 to 3 days at 40° C., the plates were replica plated and the parent plate was flooded with 0.1% Congo Red for 15 minutes. The plates were destained with 1M NaCl for 30 minutes. The strains that showed a clearing zone aroung the colony were isolated as potential cellulases producing microorganisms.

CMC-agar diffusion assay for liquid fractions

Aliquots of 40 µl of enzyme solution or fermentation broth were pipetted in wells punched out from a layer of 5 mm of minimal medium in a petri dish. After incubation for 16 hours at 40° C. cellulase activity was detected by Congo Red/NaCl treatment. The diameter of the clearing zone is a measure for the CMCase activity.

Resulting cellulase

These experiments resulted in the isolation of a cellulase producing microorganism which was deposited thereafter as CBS 670.93. The microorganism was classified as a new species of the genus Bacillus. Cloning experiments with the CBS 670.93 strain as a donor strain resulted in the isolation of an E. coli clone which was able to produce a cellulase called BCE 103. The nucleotide sequence of the gene coding for said cellulase was analysed. From the cellulase BCE 103 the N-terminal amino acid sequence was determined using standard methods for obtaining and sequencing peptides (Finlay & Geisow) (Eds.), Protein Sequencing—a practical approach, 1989, IRL Press). The amino acid sequence of the cellulase was deduced from the nucleotide sequence, using the N-terminal amino acid sequence for the starting point of the mature protein.

The nucleotide sequence for BCE 103 is shown in SEQ ID NO. 1 and the amino acid sequence is shown in SEQ ID NO. 2.

Purification of the cellulase

After the fermentation the cells were separated from the culture liquid by centrifugation (8000 rpm). The cellulase in the supernatant was precipitated with ammonium sulphate (65% saturation). The precipitate was dissolved in 25 mM phosphate buffer pH 7+5 mM EDTA until a conductivity of 7 mS/cm. This solution was applied to a Q-Sepharose FF (diameter 5 cm, length 10 cm) Anion Exchange column, after which the column was washed with 25 mM phosphate buffer pH 7+5 mM EDTA until an absorbency of 0.2 AU. A gradient of 0 to 0.5 M NaCl in 25 mM phosphate pH 7 was applied to the column in 80 minutes followed by a gradient from 0.5 to 1 M NaCl in 10 minutes. Depending on which cellulase was applied to the column, elution took place in the first or the second gradient. After elution the column was cleaned (upflow) with 1 M NaOH and equilibrated again with 25 mM phosphate pH 7+5 mM EDTA. Depending on the elution the obtained cellulase had a purity of up to about 80%.

Characterization

CMC'ase assay

Assays for cellulase activity were performed using modified methods of the PAHBAH method (Lever M. Anal. Biochem. 1972, 47, 273–279 and Lever M. Anal. Biochem. 1977, 81, 21–27).

Procedure

A test tube is filled with 250 µl 2.5% CMC in 50 mM glycine buffer pH 9 (CMC-low viscosity is purchased from Sigma) and 250 µl aliquots cellulase, diluted in the appropriate buffer. The test tube is incubated for 30 minutes at 40° C. in a waterbath, whereafter 1.5 ml of a daily fresh prepared PAHBAH solution (1% PAHBAH in 100 ml 0.5 M NaOH with 100 µl bismuth solution (containing 48.5 g bismuth nitrate, 28.2 g potassium sodium tartrate and 12.0 g NaOH in 100 ml) is added. The mixture is heated at 70° C. for 10 minutes, after which it is cooled on ice for 2 minutes. The absorption is measured at 410 nm. To eliminate the background absorbance of the enzyme samples a control experiment is executed as follows: a tube with substrate is incubated under the same conditions as the test tube. After the incubation 1.5 ml PAHBAH and the enzyme preparation is added (in this order). One unit (U) is defined as the amount of enzyme producing 1 µmol of glucose from CMC equivalent determined as reducing sugars per minute per gram product.

The buffer used for the determination of the pH/temperature profiles is a phosphate/citrate system. The pH/temperature profiles were determined using a fixed enzyme concentration which fits in the linear range of the dose response profile measured at pH 7 and 40° C. This enzyme concentration was used for the measurement of the activities under all other determined conditions.

The results for the cellulase BCE 103 are shown in FIG. 1. This cellulase shows good activities at alkaline pH, which makes it suitable for application in detergents with an alkaline pH.

Example 2

Similar procedures starting with the alkalophilic bacillus strain CBS 669.93 resulted in cellulase BCE 113. The results for this cellulase BCE 113 are shown in FIG. 2. This cellulase also shows good activities at alkaline pH, which makes it suitable for application in detergents with an alkaline pH.

Example 3

Measurement of Tensile Strength and Antipilling

As described for the evaluation of TSL, washing and experiments were performed using as detergent matrix a Colour Detergent without bleach, without perfume and enzymes (105 g detergent per wash cycle, pH10.5), as washing machine a type Miele® W 717, temperature 40° C., program „Normalprogramm", with water of a hardness of 16° dH (German hardness), wash load 3.5 kg. 25 washes.

Experiments using a composition according to the invention (D1) as well as comparisons (C1 to C3) were run in parallel in identical machines:

C1: detergent matrix without cellulase
C2: detergent matrix+0.288 mg endoglucanase V from Humicola insolens
C3: detergent matrix+cellulase mixture from Humicola insolens sold as granules Celluzyme® 0.7T
D1: detergent matrix+0.288 mg cellulase BCE 103
D2: detergent matrix+0.288 mg cellulase BCE 113

TABLE 1

| Results of TSL-measurements [%] | |
| --- | --- |
| Composition | TSL |
| C1 | 0 |
| C2 | 100 |
| C3 | 38 |
| D1 | 12 |

Using washing machines of type Miele® W 914, under otherwise identical conditions, gave the following results:

TABLE 2

| Results of TSL-measurements [%] | |
| --- | --- |
| Composition | TSL |
| C1 | 0 |
| C2 | 100 |
| D2 | 0.6 |

Example 3

Measurement of Antipilling and Calculation of the Ratio TSL to AP

The evaluation of antipilling properties was done with increased concentrations of cellulases for better quantitative evaluation of the effect. A Colour Detergent (5 g/l, 10 wash cycles at 40° C.) with the addition of cellulase as given in Table 3 was used on „pilled" sweat shirt cotton material (washed 25 times at 60° C. with a detergent without cellulase). Evaluation of the pilling was done with the optical measurement system as described before; a degree of pilling of 0% was assigned to the „pilled" material.

TABLE 3

| Results of AP-measurements [%] | | | |
| --- | --- | --- | --- |
| | degree of pilling | | |
| Enzyme concentration | EG V | BCE 103 | AP [%] of BCE 103 |
| 25 µg/ml | −12.8% | −8.4% | 65% |
| 37.5 µg/ml | −16.0% | −9.6% | 59% |
| 50 µg/ml | −22.8% | −15.6% | 68% |

An average AP of 64% can be calculated for BCE 103 cellulase. BCE 113 cellulase showed under the same conditions an average AP of 100%.

Using the values for TSL in Tables 1 and 2, the ratios of TSL to AP for the various cellulases are as in the following Table 4:

TABLE 4

| Ratio TSL to AP | |
| --- | --- |
| Enzyme | Ratio |
| EG V | 1 |
| BCE 103 | ≈0.2 |
| BCE 113 | ≈0.02 |

Example 4

Further Test Procedures

Anti redeposition test 20 ml 50% pigmented soil (fresh prepared, daily and consisting of 86% kaolin, 8% soot (Flammruss 101, obtained from Degussa AG), 4% iron oxide black and 2% iron oxide yellow (from Henkel Genthin GmbH)), in a detergent (Persil color® without enzymes, 5 g/l, pH 8.5) was, under agitating (90 ppm) incubated with white cotton fabric (prewashed, 5 cm diameter, obtained from Windelbleiche, Krefeld). Cellulase was added until a final concentration of 1 mU/ml. The mixture was incubated for 30 minutes at 40° C., 90 rpm. As a control the same incubation was carried out without the addition of cellulase. After the incubation the fabric was rinsed thoroughly with running cold water. After drying the whiteness of the fabric was measured by remission (4 measurements per fabric) using a Micro colour Dr. Lange® Colourimeter. The control value was substracted from the sample value. The results, expressed as delta Rem, are shown in Table 5.

Fibre Damage Test

One pad of cotton wool (100% cotton, Warenhandels GmbH, Buchholz, Marke Olivia, Selling agency: Aldi) was incubated in 40 ml wash liquor (Persil color® without enzyme, 5 g/l pH 8.5), cellulase at a final concentration of 1 mU/ml was added in a sealed flask and incubated for 20 hours at 40° C. under agitation (90 rpm). After the incubation, fibre damage was monitored by the measurement of the quantity of the reducing sugars in solution, using the PAHBAH method described in Example 1. As a control the same incubation was carried out without the addition of cellulase. The results are shown in Table 5.

Adsorption Test

White cotton fabric (Windelbleiche, Bielefeld) prewashed with german Persil® without enzymes at 60° C., was cut round to 9 cm diameter (approx. 0.920 gram). One cotton swatch was incubated in 50 ml 50 mM glycine-NaOH buffer pH 9 including 0.1% SDS and 1 ml cellulase sample (600 mU/ml) for 60 minutes at 30° C. 2 ml samples were taken at T=0 and at T=60 minutes and were diluted directly (1:2) with 50 mM MES-buffer pH 6.5 and stored at 4° C. until measurement. As control the same incubation was carried out without the addition of cotton textile. The activity measurement was determined with a PAHBAH method as described in Example 3, but at pH 6.5 in 50 mM MES buffer. The adsorption was expressed as relative adsorption where the activity applied at the start of the experiment was set as 100%, T=0. 100% activity value–remaining activity (%)= adsorption (%). The results are shown in Table 5.

TABLE 5

Results of the Antiredeposition Test, Fibre Damage Test and Adsorption Test

| Enzyme | Antiredeposition [detta REM] | Fibre Damage [mU] | Adsorption [%] |
|---|---|---|---|
| BCE 103 | 5.0 | 0.025 | 7 |
| KAC ®[a)] | 7.5 | 0.006 | 0 |
| EG V | 1.2 | 0.155 | 36 |

[a)]Cellualse of Kao Corporation

Cellulase BCE 113 performed in theses tests at least as well as cellulase BCE 103.

Softening test

The softness of fabrics treated as in Example 3, but after 15 wash cycles, was rated by an expert panel (5 persons) who awarded grades between 0 (fabric washed 25 times with a detergent without cellulase) and 6 (fabric prior to any wash) by the feel of the fabrics. Compositions as defined in Example 2 were used in the washings. The average rates are given in Table 6. It can be seen that the compositions according to the invention showed the best performance.

TABLE 6

Results of the Softening Test

| Composition | Rate |
|---|---|
| C1 | 0 |
| C2 | 2.1 |
| C3 | 1.5 |
| D1 | 2.3 |
| D2 | 2.2 |

---

What is claimed is:

1. A laundry detergent composition consisting essentially of 0.8 ppm to 80 ppm of a cellulase, wherein the cellulase has a ratio of tensile strength loss to antipilling properties of less than 1.

2. A laundry detergent composition according to claim 1 consisting essentially of 1 ppm to 40 ppm of the cellulase.

3. A method of laundering cotton-containing fabrics comprising contacting a cotton-containing fabric with a cellulase, wherein the cellulase has a ratio of tensile strength loss to antipilling properties of less than 1, wherein the fabric is contacted with an aqueous laundering solution consisting essentially of 0.01 mg/l to 0.2 mg/l of the cellulase.

4. A method according to claim 3, wherein the aqueous laundering solution consists essentially of 0.015 mg/l to 0.1 mg/l of the cellulase.

* * * * *

(12) EX PARTE REEXAMINATION CERTIFICATE (8397th)
United States Patent
Lenting et al.

(10) Number: US 6,313,081 C1
(45) Certificate Issued: Jul. 12, 2011

(54) DETERGENTS COMPRISING CELLULASES

(75) Inventors: Hermanus Bernardus Maria Lenting, VT Pijnacker (NL); Rudolf Franciscus Wilhelmus Cornelis Van Beckhoven, EK Breda (NL); Karl-Heinz Maurer, Erkrath (DE); Beatrix Kottwitz, Duesseldorf (DE); Albrecht Weiss, Langenfeld (DE); Pieter Van Solingen, VZ Naaldwijk (NL)

(73) Assignee: Henkel Kommanditgesellschaft auf Aktien, Duesseldorf (DE)

Reexamination Request:
No. 90/010,273, Sep. 8, 2008

Reexamination Certificate for:
Patent No.: 6,313,081
Issued: Nov. 6, 2001
Appl. No.: 08/945,574
Filed: Feb. 27, 1998

(22) PCT Filed: Apr. 26, 1995

(86) PCT No.: PCT/EP96/01755
§ 371 (c)(1),
(2), (4) Date: Feb. 27, 1998

(87) PCT Pub. No.: WO96/34092
PCT Pub. Date: Oct. 31, 1996

(30) Foreign Application Priority Data
Apr. 28, 1995 (EP) .............................................. 9520115

(51) Int. Cl.
*C12N 15/09* (2006.01)
*C12N 1/21* (2006.01)
*C12N 9/42* (2006.01)
*C12N 15/56* (2006.01)
*C12N 15/63* (2006.01)
*C11D 3/386* (2006.01)
*D06M 15/15* (2006.01)
*D06M 16/00* (2006.01)

(52) U.S. Cl. ........................ 510/320; 435/209; 510/321; 510/392; 510/393; 510/530; 8/137

(58) Field of Classification Search ........................ None
See application file for complete search history.

(56) References Cited

U.S. PATENT DOCUMENTS 5,856,165 A    1/1999    Van Solingen
6,063,611 A    5/2000    Van Solingen

FOREIGN PATENT DOCUMENTS

| EP | 0271004 | 6/1988 |
| WO | WO-91/17243 | 11/1991 |
| WO | WO-94/01532 | 1/1994 |
| WO | WO-95/02675 | 1/1995 |
| WO | WO 96/34092 | * 10/1996 |

OTHER PUBLICATIONS

Product Information for the KAO cellulase KAC–500, dated Apr. 20, 1995.

* cited by examiner

*Primary Examiner*—Alan Diamond

(57) ABSTRACT

A laundry detergent composition comprises a cellulase having a ratio of tensile strength loss to antipilling properties of less than 1. A method of laundering cotton-containing fabrics with the composition is also disclosed.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-4 are cancelled.

* * * * *